US012635973B2

(12) United States Patent
Poilvert et al.

(10) Patent No.: US 12,635,973 B2
(45) Date of Patent: May 26, 2026

(54) AUTOMATED ANALYSIS OF A PATHOLOGY BY ULTRASOUND IMAGING

(71) Applicant: Caption Health, Inc., San Mateo, CA (US)

(72) Inventors: Nicolas Poilvert, Seattle, WA (US); Kilian Koepsell, San Francisco, CA (US); Michael G. Cannon, Haverford, PA (US)

(73) Assignee: Caption Health, Inc., Waukesha, WI (US)

( * ) Notice: Subject to any disclaimer, the term of this patent is extended or adjusted under 35 U.S.C. 154(b) by 208 days.

(21) Appl. No.: 18/432,300

(22) Filed: Feb. 5, 2024

(65) Prior Publication Data

US 2025/0248683 A1 Aug. 7, 2025

(51) Int. Cl.
*A61B 8/08* (2006.01)
*A61B 8/00* (2006.01)
*G06T 7/00* (2017.01)
*G16H 30/40* (2018.01)
*G16H 50/30* (2018.01)

(52) U.S. Cl.
CPC .......... *A61B 8/0883* (2013.01); *A61B 8/5207* (2013.01); *A61B 8/5223* (2013.01); *G06T 7/0012* (2013.01); *G16H 30/40* (2018.01); *G16H 50/30* (2018.01); *G06T 2207/10016* (2013.01); *G06T 2207/10132* (2013.01); *G06T 2207/20081* (2013.01)

(58) Field of Classification Search
CPC ... A61B 8/0883; A61B 8/5207; A61B 8/5223; G16H 50/30; G16H 30/40; G06T 7/0012; G06T 2207/10016; G06T 2207/10132; G06T 2207/20081
See application file for complete search history.

(56) References Cited

U.S. PATENT DOCUMENTS

| | | |
|---|---|---|
| 8,771,189 B2 | 7/2014 | Ionasec et al. |
| 10,140,710 B2 | 11/2018 | Kreeger |
| 10,271,817 B2 | 4/2019 | Voigt et al. |
| 10,470,677 B2 | 11/2019 | Cadieu et al. |
| 10,631,791 B2 | 4/2020 | Cadieu et al. |
| 10,726,548 B2 | 7/2020 | Cadieu et al. |
| 10,806,402 B2 | 10/2020 | Cadieu et al. |
| 10,937,156 B2 | 3/2021 | Bilenko et al. |
| 11,160,510 B2 | 11/2021 | Cadieu et al. |
| 11,166,678 B2 | 11/2021 | Cadieu et al. |
| 11,207,055 B2 | 12/2021 | Keshet et al. |

(Continued)

FOREIGN PATENT DOCUMENTS

| | | |
|---|---|---|
| EP | 4091550 A1 | 11/2022 |
| WO | WO-2019075279 A1 | 4/2019 |

(Continued)

OTHER PUBLICATIONS

Wessler et al, Automated detection of aortic stenosis using machine learning. J Am Soc Echocardiogr. 36(4):411-420 (2023).

*Primary Examiner* — Chao Sheng
(74) *Attorney, Agent, or Firm* — SPQ IP LLC

(57) ABSTRACT

Methods and systems for automatic classification, detection, assessment, and/or diagnosis of a pathology in a subject determine presence or absence, and/or a severity of various pathologies in a subject, for example, presence, absences, and/or severity of aortic stenosis in a heart of a subject.

11 Claims, 13 Drawing Sheets

(56) References Cited

U.S. PATENT DOCUMENTS

| | | | |
|---|---|---|---|
| 11,497,451 | B2 | 11/2022 | Cadieu et al. |
| 11,497,475 | B2 | 11/2022 | Cannon et al. |
| 2010/0240996 | A1* | 9/2010 | Ionasec ................... G06T 7/262 |
| | | | 600/443 |
| 2015/0214434 | A1 | 7/2015 | Fujiwara et al. |
| 2018/0153505 | A1 | 6/2018 | Cadieu et al. |
| 2018/0260949 | A1* | 9/2018 | Kreeger ................ G06T 7/0016 |
| 2020/0245970 | A1 | 8/2020 | Cadieu et al. |
| 2020/0245976 | A1 | 8/2020 | Cadieu et al. |
| 2021/0052253 | A1 | 2/2021 | Cadieu et al. |
| 2021/0236094 | A1 | 8/2021 | Cannon et al. |
| 2022/0012875 | A1* | 1/2022 | Arnaout ................ G06F 18/217 |
| 2022/0104712 | A1 | 4/2022 | Sanchez Fernandez et al. |
| 2022/0104790 | A1 | 4/2022 | Cadieu et al. |
| 2023/0015122 | A1 | 1/2023 | Sun et al. |

FOREIGN PATENT DOCUMENTS

| | | | |
|---|---|---|---|
| WO | WO-2021034981 | A1 | 2/2021 |
| WO | WO-2021097460 | A1 | 5/2021 |
| WO | WO-2022241155 | A1 | 11/2022 |

* cited by examiner confidence distribution over 4 AS severities

1D CNN sequence of 10 frame embedding vectors

2D CNN sequence of 2D frames

Example Neural Network Model Architecture

AUTOMATED ANALYSIS OF A PATHOLOGY BY ULTRASOUND IMAGING

BACKGROUND

Aortic stenosis (AS) and other pathologies which can be diagnosed by ultrasound imaging are enormous public health problems that affect more than 12.6 million adults and worldwide causes an estimated 102,700 deaths annually. Recently, there has been interest in earlier identification of AS and evidence that many patients may not be appropriately treated. These observations motivate the study of novel methods to identify AS and other pathologies, however, little is currently known about how to improve the identification and treatment of AS. Using a population-based comprehensive transthoracic echocardiographic (TTE) screening approach would be prohibitively expensive. Automated interpretation of limited echocardiographic data sets is an attractive alternative approach to disease detection, especially with the rise of point-of-care ultrasound devices. Barriers to automating AS (and other pathology) detection relate to the complex nature of these diagnoses, the need to integrate information across multiple images for any given study, and data sets that are not routinely annotated as part of routine clinical care in addition to the high complexity of even routine echocardiographic assessment of AS which often uses all standard imaging modes and multiple scanning views and windows. Results for conventional detection of AS are therefore highly dependent on the skill of the ultrasound operator, particularly in making measurements of two dimensional structures, and producing optimized Pulsed and Continuous Wave Doppler signals.

Another major difficulty with AS detection is the long asymptomatic period of AS. During that time, the disease progresses, most often unbeknownst to the patient. Given the level of expertise currently required to diagnose AS, most patients first learn about their condition after a full echocardiographic study has been performed, usually upon referral from their primary care physician because symptoms have already started to appear. The dramatic consequence is that many patients are left undiagnosed simply because they don't exhibit symptoms. Moreover, the diagnosis is often established later in the course of the disease. Symptomatic severe aortic stenosis is associated with high mortality rates, up to 50% at 1 year, and the prevalence will likely increase as the population ages. Accordingly, improved methods and systems for early detection of AS and other pathologies are needed.

SUMMARY

In one aspect, described herein, are methods for ultrasound imaging. In some aspects, the methods comprise acquiring a plurality of ultrasound images of at least a portion of an organ of a subject using an ultrasound imaging system. In some aspects, the plurality of ultrasound images comprises images captured across at least a portion of at least one full heart cycle.

In some aspects, the methods comprise processing the acquired plurality of ultrasound images to automatically classify a pathology of the subject comprising providing the acquired plurality of ultrasound images as input to a trained machine learning model. In some aspects, the methods comprise outputting an indication of a condition of the subject.

In some aspects, the outputting is based at least in part on an output of the trained machine learning model. In some aspects, the output comprise: (i) an indication of presence or absence of the pathology in the subject; and/or (ii) a confidence estimate of the indication of (i).

In some aspects, the machine learning model is trained by a training method which does not comprise landmark computer vision analysis of tissue and/or manual labelling of training data with heart phase information. In some aspects, the indication of (i) further comprises an estimation of a severity of the pathology. In some aspects, the pathology is aortic stenosis, and the organ is a heart of the subject.

In some aspects, the method does not comprise visual detection of a heart valve closure within the acquired plurality of images. In some aspects, the automatic classification is performed on at least a subset of the plurality of ultrasound images which are substandard images. In some aspects, the training method comprises individually assessing prediction accuracy of each of a plurality of discreet views comprised in at least a subset of the training data.

In some aspects, the plurality of discreet views comprises standard views and non-standard views. In some aspects, one or more video clips comprise the acquired plurality of ultrasound images. In some aspects, the processing comprises sliding a window across a plurality of frames of the one or more video clips to select frames which provide an improved confidence of the indication of (i) compared to an indication based on an indication generated using a stationary window comprising a single heart cycle. In some aspects, the frames of the one or more video clips comprise frames acquired from more than one heartbeat. In some aspects, the sliding window is slid across frames from more than one heart cycle.

In some aspects, each of the one or more video clips is associated with one or more discreet views. In some aspects, estimating the severity of the pathology comprises, for each of the one or more video clips: determining a heart period of the subject of the video clip; sliding a window of a size based on, the determined heart period over the clip; and/or computing a confidence distribution and/or an associated likelihood of successful severity classification for the pathology.

In some aspects, estimating the severity of the pathology comprises extracting windows associated with the one or more video clips which meet a threshold value for likelihood of successful severity classification. In some aspects, estimating the severity of the pathology comprises combining the extracted windows from two or more of the one or more discreet views to obtain an increased likelihood of successful severity classification compared with classification based on an individual one of the discreet views.

In some aspects, any method step described herein can be repeated for all view supported by the ultrasound imaging system. In some aspects, the ultrasound imaging system supports 30 or more views.

In some aspects, estimating the severity of the pathology further comprises: ranking the windows for all clips associated with a particular view based on likelihood of successful severity classification to obtain a subset containing less than all of the windows associated with the particular view, which comprises three or more windows associated with the particular view which have the highest likelihood of successful severity classification; and after the combining of the extracted windows, re-ranking the windows for all of the combined clips based on likelihood of successful severity classification to obtain a combination of windows having a highest global likelihood of successful severity classification.

In some aspects, the output comprises an instruction of a user of the ultrasound system to acquire further images of the subject. In some aspects, the instruction to acquire further images is provided based at least in part on a detection of at least a threshold likelihood of a presence of the pathology in one or more of the acquired plurality of ultrasound images. In some aspects, the instruction to acquire further images is provided based at least in part on a detection that less than a threshold confidence in the presence or absence of the pathology is detected.

In some aspects, the acquired plurality of ultrasound images are two-dimensional ultrasound images. In another aspect, described herein are non-transitory computer-readable media, storing instructions that, when executed by a processor of a computer, cause the computer to perform any of the methods described herein.

In another aspect, described herein, are ultrasound imaging systems. In some aspects, the ultrasound imaging systems comprise an ultrasound imaging probe and a computing system. In some aspects, any of the ultrasound systems described herein can be configured to perform any of the methods described herein. In some aspects, the ultrasound imaging systems can further comprise any of the non-transitory computer-readable storage media described herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative aspects of the present disclosure are shown and described. As will be realized, the present disclosure is capable of other and different aspects, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative aspects, in which the principles of the invention are utilized, and the accompanying drawings (also "Figure" and "FIG." herein), of which:

DETAILED DESCRIPTION

Figure 1A:
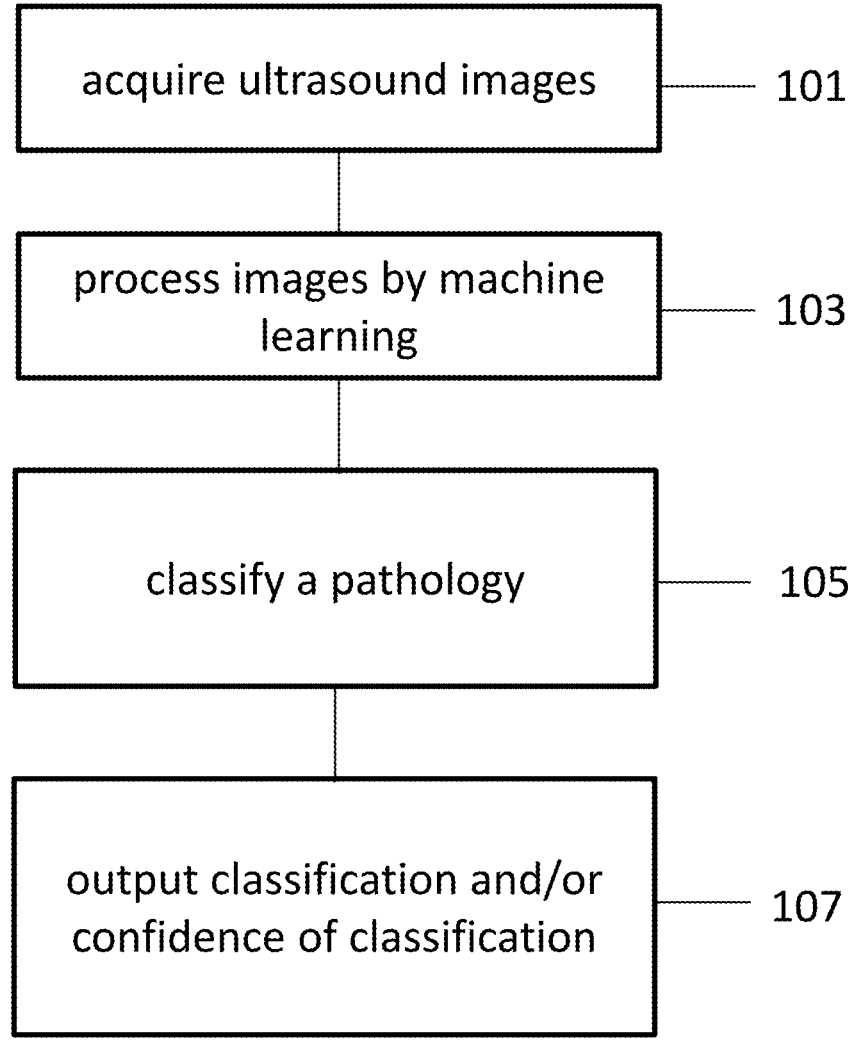
FIG. 1A illustrates an example workflow for automatic classification of a pathology according to methods and/or using systems described herein.

While various aspects of the invention have been shown and described herein, it will be obvious to those skilled in the art that such aspects are provided by way of example only. Numerous variations, changes, and substitutions may occur to those skilled in the art without departing from the invention. It should be understood that various alternatives to the aspects of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Certain inventive aspects herein contemplate numerical ranges. When ranges are present, the ranges include the range endpoints. Additionally, every sub range and value within the range is present as if explicitly written out. The term "about" or "approximately" may mean within an acceptable error range for the particular value, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Where particular values are described in the application and claims, unless otherwise stated the term "about" meaning within an acceptable error range for the particular value may be assumed.

Diagnostic Image Quality

A particular challenge in ultrasound medical imaging is accurately determining what probe pose or movement will result in a clinical or diagnostic quality image. As used herein, an image quality (e.g. diagnostic quality or clinical quality) may be used to refer to one or more aspects of the quality of an image. In some aspects, image quality is in reference to an image that can be viewed by a trained expert or a machine learning tool in a way that anatomy is identified and a diagnostic interpretation can be made. In some aspects, image quality is in reference to an image in which the targets are displayed in a clear and well-defined manner, for example, where extraneous noise or clutter is minimal, the grayscale display shows subtle variations of tissue type and texture, blood flow signals are clear and distinct, frame rates are high, providing accurate depiction of tissue or blood flow movement, borders between tissue types or blood flow and vessel or other structures are well resolved, ultrasound artifacts such as grating and side lobes are minimized, acoustic noise is absent, places to make measurements in the image are obvious and distinct, or any combination thereof depending on the nature of the ultrasound exam. In some aspects, image quality is in reference to an image that contains the necessary anatomical targets to represent a standard diagnostic view. For example, an Apical Four Chamber view of the heart should show the apex of the heart, the left and right ventricles, the myocardium, the mitral and tricuspid valves, the left and right atria, and the interatrial septum. As another example, a long axis view of the carotid artery at the bifurcation should show the common, external, and carotid artery and the carotid bulb. In some aspects, image quality is in reference to an image in which a diseased condition, abnormality, or pathology is well visualized. For example, medical images may be labeled by cardiologists, radiologists or other healthcare professionals according to whether they are considered to have a well visualized diseased condition, abnormality, or pathology, and then used to train a machine learning algorithm to differentiate between images based on image quality.

In some aspects, image quality means that some combination of these aforementioned characteristics is present. Effective navigational guidance will need to be provided to ensure the captured ultrasound image satisfies the combination of these image quality characteristics necessary to yield an overall clinical or diagnostic quality image because, in ultrasound imaging, patient presentations can present challenges to obtaining high-resolution, low-noise images. It can be particularly challenging, for example, when trying to evaluate blood flow in the kidney of an obese agent, to get a strong enough blood flow Doppler signal because the kidney is so deep underneath fatty tissue. In a patient who has been a long-term smoker, lung disease can make it very difficult to obtain high quality cardiac images. These conditions are extremely common, and in such situations, image quality can mean an image that may be sub-optimal as far as noise and resolution, but still provides enough information for a diagnosis to be made. In a similar way, patient presentations and pathologies can make it impossible to obtain views that show all the anatomical components of a standard, canonical image. For example, a technically difficult cardiac patient may make it impossible to get an Apical Four Chamber view with all four chambers well defined, but if some images show, say, the left ventricle well, this can be considered a quality image because many critical diagnostic conclusions can be drawn from only that.

In some aspects, the anatomical views used in the present disclosure include one or more of a probe position or window, an imaging plane, and a region or structure being visualized. Examples of probe position or window include parasternal, apical, subcostal, and suprasternal notch. Examples of imaging plane include long-axis (LAX), short-axis (SAX), and four-chamber (4C). Examples of the region or structure being visualized include two-chamber, aortic valve, mitral valve, etc. For example, the anatomical views can include parasternal long-axis (LV inflow/outflow), RV inflow+/−RV outflow, parasternal short-axis (aortic valve level, mitral valve level, papillary muscle level, apical LV level), apical four-chamber, apical five-chamber, apical two-chamber, apical three-chamber, subcostal four-chamber view, subcostal short-axis and long-axis, suprasternal long-axis (aortic arch) and suprasternal short-axis (aortic arch).

Substandard Images

As used herein, "substandard" images may be off-axis views, views incomplete anatomy shown, and/or non-canonical views. In some cases substandard images may be substandard due to low image quality. In some aspects, the quality may be low because of user inexperience, incorrect ultrasound device settings, and/or patient body type such as narrow rib spaces or obesity. In certain cases, substandard images may have substandard quality where the quality is considered low compared to an ideal, high quality image because of the presence of a pathology causing acquisition of an image that is difficult to interpret because of noise or artifacts. In some instances of substandard images, conventional automated image analysis or image quality analysis methods may reject the substandard image and not include it in the automated processing of pathology (e.g. valve stenosis) estimation.

Standard and Non-Standard Views

Some examples of standard and non-standard views that can occur with ultrasound imaging of the aortic valve: the parasternal long axis view of the aortic valve in a standard, high quality example will display numerous features of the heart not just the aortic valve. That is, it will show the left ventricle cavity, left ventricle myocardium, mitral valve, left atrium, portions of the right ventricle, and the aortic valve. In the standard view, the aortic valve will appear at the right edge of the image. A nonstandard PLAX view that is good for assessing the aortic valve may exclude the anatomical structures that are not the aortic valve, instead just show the aortic valve. In this instance the valve may be in the middle or even opposite edge of the image compared to the standard orientation. Conventional image assessment algorithms may reject this type of image because it is so different from textbook images.

Basic echo views that display the aortic valve, such as the parasternal long axis, parasternal short axis, and apical five chamber view, ideally show the aortic valve leaflet structures and their movement clearly. The visualization of the leaflets can inform the assessment of stenosis and stenosis severity. If the leaflets are non-thickened by calcific or other lesions and if they move freely, opening fully, then stenosis may be ruled out. However, if the valve leaflets are stenotic and diseased then their movement may be abnormal and the open orifice during systole may be reduced. In these instances speckle noise and shadows caused by the calcific valve can produce poor quality images that do not have the standard appearance or clarity of an optimal image.

As used herein, "standard" views generally refer to the textbook image (e.g. for canonical view), whereas a "non-standard" view generally refers to an image which deviates from the textbook image, while still showing one or more features of interest which are relevant to classification of the pathology being assessed by the methods described herein.

Classification of Pathology

Described herein are methods and systems which provide an accurate, fast, simple, and/or low-cost method for assessing pathologies by ultrasound imaging, for example cardiac valvular stenosis. In some cases such assessment can be performed using two-dimensional imaging. In certain instances, the pathology classified is aortic stenosis and or stenosis of other valves of a hear of a subject.

Classification can be performed using a variety of possible workflows as described herein, for example, as illustrated in FIG. 1A. A sonographer, a cardiologist, or other user may acquire ultrasound images of a subject or patient 101, for example, by retrieving them from a data storage medium, from a data storage medium of an ultrasound imaging system or by directly acquiring them from a patient being imaged in real time using an ultrasound imaging system. The images are then processed 103, for example by a machine learning model operating directly on an ultrasound imaging system, or by another system where the images were retrieved in 101. One or more pathologies are then classified by the machine learning model or algorithm 105, and an output is provided to the user 107, for example, the output may comprise a severity and/or a confidence value for the estimation of the severity. In some cases, the output may comprise an identity of a detected pathology.

Figure 1B:
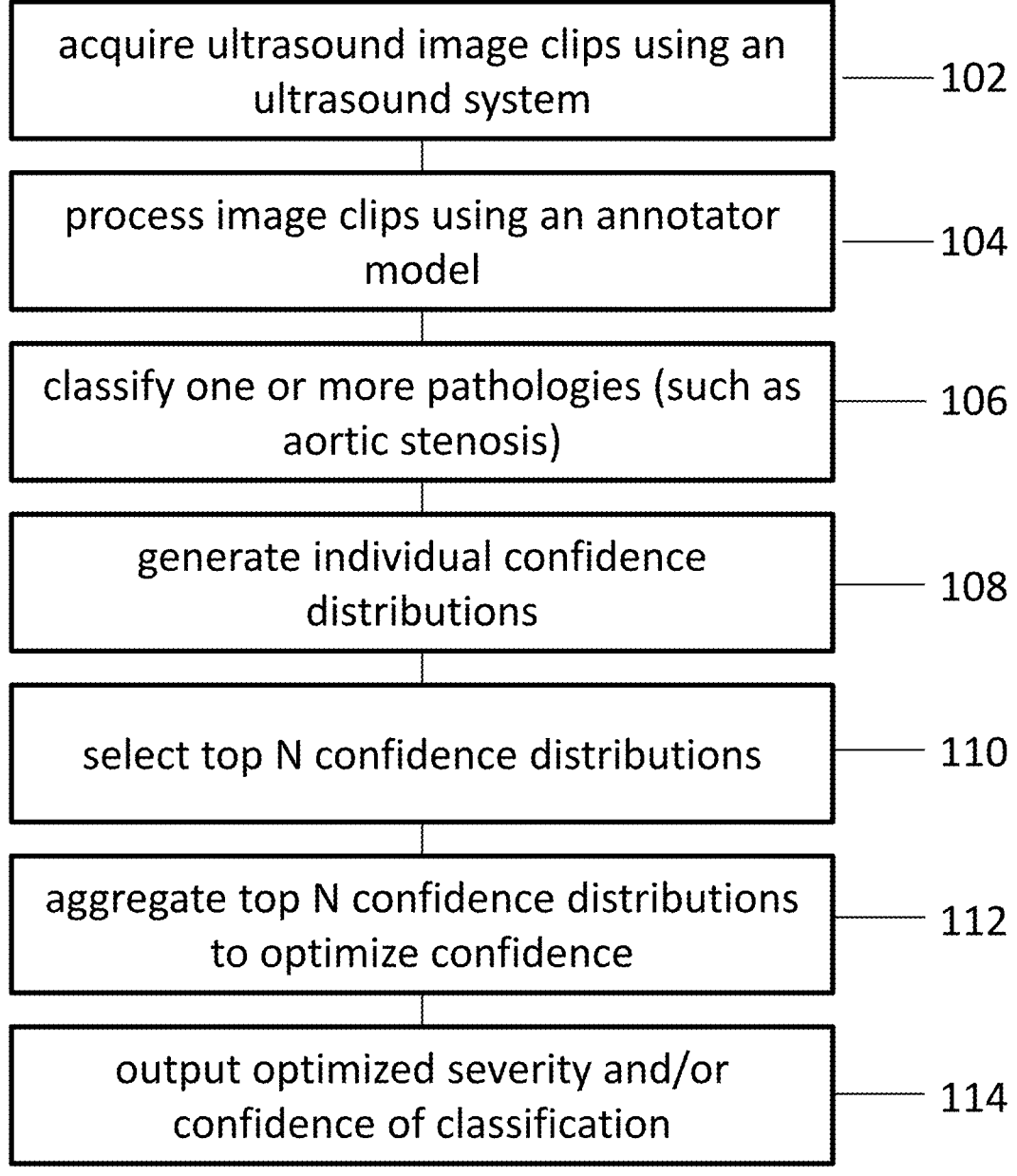
FIG. 1B illustrates an alternate example workflow for automatic classification of a pathology (such as aortic stenosis) according to methods and/or systems described herein.

Alternate workflows can include any combination of features or method steps described herein. For example, as illustrated in FIG. 1B, a sonographer, a cardiologist, or other user may acquire ultrasound image clips of a subject or patient by directly acquiring them from a patient being imaged in real time using an ultrasound imaging system 102. The images clips can then be processed using an annotator model to classify individual views, for example, using a 2D convolutional neural network 104. One or more pathologies are classified by annotator an a sub-view by sub-view basis 106, and individual confidence distributions are generated for each pathology and/or each sub-view being classified 108. Combinations and/or subsets of the individual confidence distributions are evaluated and the top N (e.g. top 3, top 10, top 15, etc.) are selected 110, and aggregated 112 to produce a combined confidence distribution which is optimized for confidence of classification of one or more pathologies. Images collected from the subject in 102 are then evaluated using the optimized confidence distribution, and an output of the optimized computed severity and a confidence value of the estimation is provided to the user 114. In some cases the output may comprise identification of a plurality of pathologies, and/or their severities (where more than one pathology is detected in the acquire images). Training may be performed using a rich and diverse training data set. In some cases a 2D neural network in aspatial domain is utilized together with a 1D neural network in a temporal domain. In some instances, a third neural network is utilized as an annotator for preprocessing using transfer learning with pretrained weights from the annotator may be used to initialize a spatial part of a model. In some cases, the model is trained to multitask using an auxiliary heart cycle regression function to teach the model to predict the moment of the heart cycle for each individual frame. In some aspects, a gaussian mixture is fit to empirical data distribution of aortic stenosis severity in the measurement space (the three-dimensional space of parameters such as aortic valve area, mean pressure gradient of flow, and peak jet velocity). Severity level probabilities returned. A Probability Mass Function is used to represent likelihood of each level.

An example model architecture utilizes a cascade of two CNNs in two domains, which runs on 24 contiguous frames that can be in a sliding window. MobileNetV3. Each frame individually processed by a 2D network into a 1D embedding vector. That is processed along the time axis in 1D. An example, Auto Aortic Stenosis Service 1) Image Preprocessing: Pixel standardization and rescaling. Frames processed along time axis to add auxiliary dynamic frames for temporal features. 2) the example annotator: First step in process. Recognizes view, scan mode, and heart cycle period. Filters for minimal clip lengths. Can assign image quality grade and other attributes. Clips are run through the example annotator to select ones eligible for AS severity assessment. 3) Prediction of Heart Cycle Period of an Image: Initial algorithm implementation uses a trained neural network with EKG trace as an input, other image-based methods can be used or combined with this. Determines R-wave to R-wave periods. 4) Aortic Stenosis Prediction: Model produces a Confidence Distribution of AS severity levels. It can also predict other related parameters such as valve area, mean pressure gradient, peak jet velocities, etc., from the 2D (B-Mode) image. Confidence Distribution can be averaged over multiple heart cycles and can use and combine multiple views. 5) Probability of Successful Classification Quantification: Uses two features: maximum value of Confidence Distribution and concentration of the distribution around the maximum value. Plotted to produce a scalar that serves as a Probability of Success Quality Score. High scores are associated with a high probability of making no errors.

C) Interoperability with Standard Machine Learning Image Quality Scoring and Clip Selection When implemented to run integrated into an AI real-time acquisition device such as our guidance products, the AS Severity Score outputs can run in real-time and be weighted with standard image quality assessment scores to allow images that have a high pathology detection probability not to be rejected by the image quality clip selection function that may be looking for common canonical high quality images and not be trained to accept non-canonical images that include pathologies. This can be done without specific training of the model for this discrimination. This function can also run on images that have already been acquired, such as on a PACS viewer.

Accurate automated classification of aortic stenosis severity can be performed from just 2D images. In some cases, a standard image quality clip selector function is not required to identify clips for processing. In such cases, abnormal images that would not meet standard image quality definition are not rejected for processing. In such cases, the algorithm can assess prediction accuracy of an image that is independent of conventional image quality, does not need clip selector to be trained separately for pathology. This aspect may also be important and unique when integrated into an ultrasound imaging system that includes scan acquisition guidance, but is also valuable running on already-acquired images.

In some instances, models described herein can be trained without requiring landmark computer vision analysis of tissue and without requiring manual labelling of training data heart phase information. In such instances, the heart phase information can be determined directly from analysis of one or more ultrasound images. Such methods can provide distinct advantages compared with earlier non-EKG methods. For example, methods that are based on valve closure detection might suffer from poor image quality, particularly when the patient has a stenotic valve or valves. In some instances, a sliding window can use frames from more than one heart cycle, including a time interval of one heartbeat where the frames making up that interval are from portions of two separate heartbeats.

In some instances, methods described herein comprise estimation of severity of a pathology such as aortic stenosis comprising: For each distinct clip associated with a given view, the approach is the following: 1) Determining the patient's heart period on that very clip using a machine learning model; 2) Sliding a window of the size of the heart period over the clip. For each window, computing the AS confidence distribution and its associated likelihood of successful severity classification; 3) Extracting the top N such windows (based on the likelihood); 4) Once the above has been done on all clips associated with a given view, ranking all top N windows across all clips; 5) Repeat the above procedure for all supported views; and 6) Combining the top N windows "across" all views and recompute the likelihood values based on view combinations. Re-rank all window combinations and return the combination with the highest likelihood of successful severity classification.

Described herein are methods for early detection of pathologies such as aortic stenosis. In some cases, methods can be used to provide a tool that can conveniently help identify cases of Aortic Stenosis, in adults before the aortic stenosis becomes symptomatic (e.g. detecting AS during its asymptomatic period). In some cases, methods and systems described herein can allow for screening and/or assessment of patients exhibiting a number of risk factors are present (like advanced age, presence of a murmur, pathological findings like a bicuspid aortic valve), by non-specialists such as a family physician. If this initial assessment suggests the possibility of moderate to severe AS, the patient would then be referred to an echocardiography laboratory since moderate to severe AS have markedly elevated risks of poor outcomes when compared to mild or no AS.

Example Implementation

An example model described herein was built with that scenario in mind. Patient data selected for evaluation of the model was derived from two institutions: Northwestern Medicine (NM), with at least 4 distinct acquisition sites and Minneapolis Heart Institute (MHI), with at least 39 distinct acquisition sites, from rural clinics to academic centers.

Given the relatively low prevalence of mild, moderate and severe AS in echo databases, echocardiographic studies were selectively sampled to enrich datasets with as many AS cases as possible. For each study, the following information was gathered when available:

AS severity, as determined by the original reading cardiologist, and established following ASE/ACC guidelines about quantification of AS Aortic Valve Area (AVA) (typically by the Continuity Equation method)

Peak Aortic Valve Velocity (also known as Jet Velocity—JV)

Mean Pressure Gradient (MPG) across the aortic valve

Any information indicative of the presence of an artificial aortic valve (TAVR, mechanical valve)

Sex, height, weight and age of the patient

Ultrasound machine model

Morphology of aortic valve leaflets (tricuspid, bicuspid)

This initial extraction yielded a pool of just over 200,000 studies to choose from. Training data was then constrained to the following requirements:

Patients should have their native valve in place (so no patients with an artificial aortic valve). This requirement was imposed to account for the fact that artificial aortic valves usually lead to elevated hemodynamic parameters (values of JV and MPG in particular) when compared to natural valves, which could potentially confuse the model and lead to systematic bias in severity prediction.

Patients should have at least one of AVA, MPG or JV available or have an AS severity label available Patient sex, age, weight and height should be available most of the time Ultrasound machine model should be available all the time These constraints restricted the set of allowed studies to about 80,000. All data points from those studies that had an aortic stenosis severity greater than "none" were then used to train the model. To complement these, a subset of "none" AS studies were randomly sampled with a view to maximize diversity over the following characteristics: sex, BMI, ultrasound machine models and number of unique patients.

The final development datasets obtained contained:

Evaluation dataset characteristics: 1,771 unique studies from 1,427 unique patients 1,158 unique studies from 999 unique patients originating from MHI; 613 unique studies from 428 unique patients originating from NM; 852 studies from Female patients, 919 studies from Male patients; No patients in common with the training dataset described below Breakdown by BMI (there were 15 studies for which either height or weight or both were not available from patient records): BMI Normal (BMI<25) Overweight (25≤BMI<30) Obese (30≤BMI): studies 543|546|667.

Breakdown by Manufacturers:

Manufacturer GE Philips SIEMENS Studies

202 Vivid E95

118 Vivid E9

115 Vivid i

20 Vivid7

440 iE33

113 CX50

44 EPIQ 7C

510 SEQUOIA

209 ACUSON SC2000

Acquisition Years:

Year: 2008|2009|2010|2011|2012|2013|2014|2015| 2016|2017|2018|2019|2020

Studies: 29|65|69|34 83|174|227|278|199|39|264|277|33

The evaluation dataset was built as a representative set of AS severities. Specifically, the breakdown by AS severities was:

AS severity: None|Mild|Moderate|Severe

Studies: 1,409|248|57|57

Training Dataset Characteristics:

29,527 unique studies from 26,981 unique patients 12,418 unique studies from 11,245 unique patients originating from MHI 17,109 unique studies from 15,736 unique patients originating from NM 14,856 studies from Female patients, 14,671 studies from Male patients Breakdown by BMI:

BMI Normal (BMI<25)|Overweight (25≤BMI<30) |Obese (30≤BMI) studies 8,846|9,761|10,711

Breakdown by Manufacturers:

Manufacturer GE Philips SIEMENS Studies 7,749 Vivid E95

3,698 Vivid E9

2,725 Vivid i

197 Vivid7

7,117 iE33

1,347 CX50

641 EPIQ 7C 4,290 SEQUOIA 1,763 ACUSON SC2000

Acquisition Years:

year 2008|2009|2010|2011|2013|2014|2015|2016|2017| 2018|2019|2020 studies 132|347|481|737|1,389|2,059|2,016|5,257|1, 638|6,527|7,838|1,106

For about 97.5% of these studies (28,787 in total), access to the original AS severity diagnosis was possible with the following breakdown:

AS severity None|Mild|Mild to Moderate|Moderate- |Moderate to Severe|Severe studies 20,622|3, 015|718|1,667|1,035|1,730

For the remaining 2.5% (740 in total), Doppler-derived measurements (AVA, MPG and JV) were available. The fact that original AS severities for all patients was not present in the training dataset did not pose a problem as is discussing in detail below.

Training Methodologies

Assembling a large and diverse training dataset is only the first step. The ways in which the model is trained are also important, particularly to reduce bias in model predictions.

Outlined below are techniques used to reduce the chances of overfitting, improve generalization and combat model bias in the example model:

Model capacity was purposefully limited. The example model was a sequence of a lightweight 2-dimensional convolutional neural network core operating in the spatial domain, followed by a 1-dimensional convolutional neural network operating in the time domain. In particular, the use of 3-dimensional convolutional architectures was avoided to reduce computational burdens associated with a prohibitive parameter count and generally increased computational cost, and also to reduce overfitting. To further reduce overfitting and improve generalization stochasticity was injected at different levels.

Specifically, heavy Dropout regularization was used while at the same time training the model using small batch sizes (16 or 32). Further, the model was trained using a fine-grained oversampling strategy.

24 buckets of studies were created corresponding to the cartesian product of 2 patient sex buckets, 3 ultrasound manufacturer buckets and 4 aortic stenosis severity buckets (in total 2×3×4=24 buckets). During training, examples were sampled randomly and uniformly from these 24 buckets. As such, the model was presented with data from male patients 50% of the time and from female patients the other 50% of the time. Similarly, ⅓ of the time the model was presented with data from GE machines, ⅓ of the time with data from Philips machines and ⅓ of the time with data from SIE-MENS machines. The same goes for AS severities, with each of the four severities presented 25% of the time.

The example model training strategy was successful minimize bias in model predictions against several characteristics of interest (here patient sex, ultrasound machine type and level of aortic stenosis severity).

Figure 6:
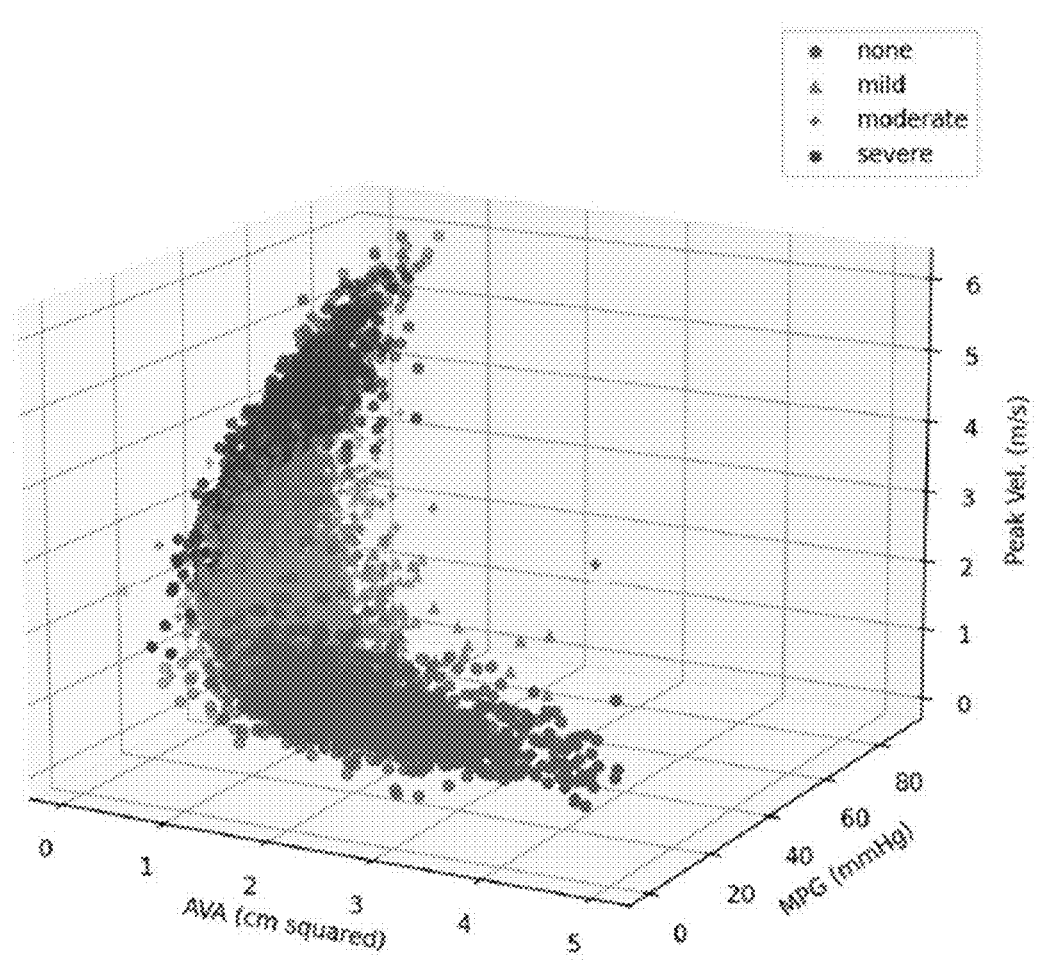
FIG. 6 illustrates a scatter plot displaying empirical aortic stenosis severity densities in measurement space for an example implementation of methods and systems described herein, which were implemented in accordance with the example workflow illustrated in FIG. 3.

To further improve model performance, transfer learning and pretrained weights were used to initialize the spatial part of the example model (while the temporal part was initialized at random). These pretrained weights came from an annotator model described such as those described herein. Another performance improvement came about after the example model was trained to multitask. An auxiliary task of heart cycle regression was added to teach the model to predict the exact moment of the heart cycle on each frame. In some cases, knowledge distillation is used to exclude the use of one-hot encoding labels as supervisory signal to train the example model. Instead, a Gaussian Mixture is fit to each AS severity's empirical data distribution in measurement space (the 3-dimensional space of AVA, MPG and JV). As can be seen in FIG. 6, AS severity densities were well behaved in that space. For each study in the training set, the associated triplet (AVA, MPG, JV) was used and fed to each of the Gaussian Mixtures to obtain 4 positive values (each Gaussian Mixture returned the value of its probability density for that input triplet). Bayes rule was then used to derive a Probability Mass Function (PMF) that represented the likelihood with which the input triplet came from any of the 4 AS severities. That PMF, in turn, was used as a supervisory signal to train the example model using a straightforward cross entropy loss.

Figure 2:
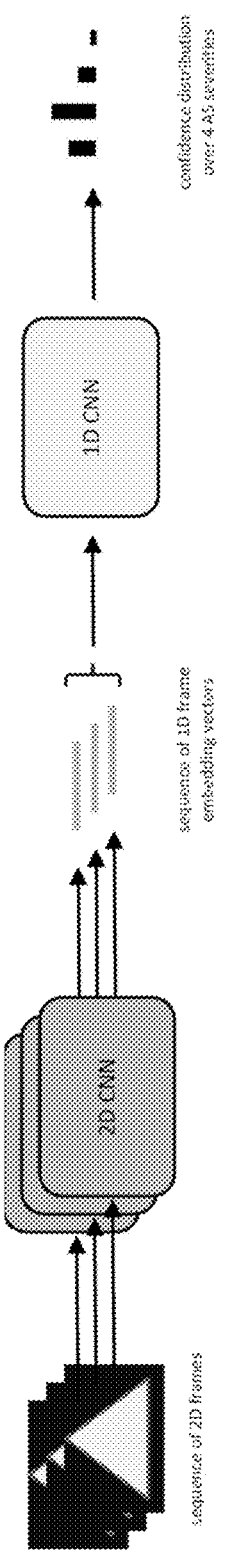
FIG. 2 illustrates an example model architecture which can be used to implement aspects of methods and systems described herein.

In some cases, use of these "smooth" labels improved overall performance as well as reduced variability in predictions. The example model used a cascade of two convolutional neural networks operating in different domains (see FIG. 2). An input sequence of 24 contiguous video clip frames was fed to a 2D convolutional neural network (CNN). The network's architecture was MobileNetV3 Large. Each frame in the sequence was independently processed by this 2D network into a 1D embedding vector. The resulting sequence of 1D frame embeddings was then processed along the time axis by another 1D convolutional neural network. That later network was made up of an initial dimensionality reduction operation (reducing the size of the feature space of embeddings from 1,280 down to 256) followed by a sequence of 2 residual blocks, each block being made up of 2 1D convolutions in series followed by a residual connection. Finally, a last dimensionality reduction operation (from 128 dimensions down to 64) was inserted. All 1D convolutions used in the example had kernels of size 5. FIG. 2 details the architecture of the example model's temporal CNN.

The example model illustrated in FIG. 2 comprises a cascade of two convolutional neural networks operating in different domains. An input sequence of 24 contiguous video clip frames is fed to a 2D convolutional neural network (CNN). The network's architecture utilized MobileNetV3 Large. Each frame in that sequence is independently processed by this 2D network into a 1D embedding vector. The resulting sequence of 1D frame embeddings is then processed along the time axis by a 1D convolutional neural network. That later network is made up of an initial dimensionality reduction operation (reducing the size of the feature space of embeddings from 1,280 down to 256) followed by a sequence of 2 residual blocks, each block being made up of two 1D convolutions in series followed by a residual connection. Finally, a last dimensionality reduction operation (from 128 dimensions down to 64) is inserted. All 1D convolutions have kernels of size 5.

Operational Details of the Example Model Service for Assessing Aortic Stenosis The example model was implemented as part of a service that provides an end-to-end software system that processes an entire echocardiographic study on its own and produces an estimate of aortic stenosis severity as output. This service included two main models: an annotator and the example model itself.

Image Preprocessing

Both the annotator and the example model were implemented to operate directly on ultrasound image files. These images may be in a number of formats. For training and development, video clip images were used. These were typically obtained in a DICOM format. Other image formats could be used for algorithm training and development. For example, scan converted video images that have not been converted into a full DICOM-compatible format may also be used by the example model in addition to or as a replacement for DICOM-formatted images.

In some cases, pre-scan converted polar coordinate images can be used. To address this variety, the terms images, clips, or video are used interchangeably. Before these files can be fed into the annotator or the example model several transformations may need to be applied. For example, image content may first be extracted from the image file and decompressed into a 4-dimensional tensor of RGB frames representing a video clip. The dimensionality of this tensor may be [N, H, W, 3], where N represents the number of frames in the video clip, H and W are respectively the height and width in pixels of each frame and 3 represents the number of color channels. The data type can be implemented as uint8 (unsigned byte). Given the input tensor, the number of frames, N, may be checked for being greater or equal to a threshold window size (for the example model this was implemented as 24). The example model operates on time windows of 24 consecutive video frames, and if the clip is not long enough, it is rejected.

Next the a determination can be made as to whether the image file contains the necessary information that identifies the location of the ultrasound cone area. The vast majority of image files that display an active ultrasound region of interest save this information inside a metadata field called a "Sequence Of Ultrasound Region" (SOUR). If this information is unavailable, the clip is rejected, otherwise the cone area is cropped out of the full frames.

The cone area clip color frames can then be transformed into grayscale frames using a dot product operation along the channel dimension for respectively red, green and blue channels. Once grayscaled, the frames can then be quantized back into uint8. The grayscaled frames can subsequently be scaled to a height of 256 pixels while keeping aspect ratio intact (resizing for the example model was performed in uint8). A 256-pixel wide section can then be cropped along the width of the frame centered about the middle vertical line (so that the "tip" of the cone area stays in the middle). Finally, from the resulting 256×256 square, the central 224×224 part was extracted.

Pixels can then be standardized in a number of ways. For the example model, the first standardization was a simple rescaling of pixel values from the original uint8 range, namely [0, 255], to [0, 1] by multiplying all the frames by $\frac{1}{255}$. The resulting standardized frames are referred to as appearance frames herein. A second standardization leverages the periodicity of heart beats. First, The mean temporal image is extracted by averaging all frames in the clip (averaging across the frame index or "time" dimension). Second, the mean temporal image is subtracted from each frame in the clip. Finally, the resulting (centered) frames are multiplied by a pre-computed scaling factor so that the expected standard deviation in pixel values be one. The resulting standardized frames are referred to herein as the dynamic or temporal frames.

For each frame in the original clip, two distinct standardized frames are obtained: an appearance frame and a dynamic frame. As a final step, these standardized frames are concatenated along the channel dimension.

Example Annotator Model

Before an image can trigger a response from the example model which classifies aortic stenosis, it is first processed by an annotator model. The annotator model's role is to recognize both the mode (B-mode or Color Flow Doppler) and the view (echocardiographic view) of the clip.

The example annotator is a 2D CNN architecturally identical to the spatial part of the example model for classifying aortic stenosis (i.e., MobileNetV3 Large). It was trained using a multitask learning approach on a very large dataset. Specifically, the annotator was trained to jointly predict the following set of attributes on each frame:

Patient sex

Patient age

Patient BMI

Echocardiographic mode (either B-mode or Color Flow Doppler)

Echocardiographic view (one of 48 possible views)

Set of physiological features present in the image (from a set of 26 possible features, like aortic valve, mitral valve, left ventricle, right atrium, left ventricular outflow tract, hepatic veins, etc. . . . )

"Echo Distances" (ground truth echo distances were computed using an AI guidance model). As used herein, echo distances generally refer to a deviation between a contemporaneous ultrasound probe pose, and an ideal pose determined by an AI probe guidance model.

Heart Cycle coordinates

The training dataset for the example annotator consisted of 452,778 image files (each contributing 20 randomly sampled frames for a total of more than 9M individual frames) extracted from 45,783 unique studies originating from 35,262 unique patients. In a manner similar to what was done with for the example model for classifying aortic stenosis, the example annotator model was trained using a fine-grained oversampling approach using a total of 144 buckets (2 patient sex buckets times 3 patient BMI buckets times 3 ultrasound manufacturer buckets times 8 patient age buckets).

The example annotator training dataset overlapped with the training dataset of the example aortic stenosis model with the following breakdown:

22,188 patients were unique to the example aortic stenosis model's training dataset 30,469 patients were unique to the example annotator's training dataset 4,793 patients were common to both training datasets Crucially, none of the patients to be used in validating the example aortic stenosis model are in common with the example aortic stenosis model's training dataset, the example annotator's training dataset or the example aortic stenosis model's evaluation dataset.

Clip Processing Acceptance Criteria

For the example aortic stenosis model to return an aortic stenosis severity prediction, input image files must satisfy a number of conditions. These conditions are:

image clip must successfully be preprocessed as outlined previously the example annotator needs to recognize the clip as B-mode. Color Flow Doppler clips are rejected the example annotator needs to recognize one of the supported cardiac views (e.g. in the example implementation PLAX, PSAX-AoV or AP5), other views are rejected.

The example aortic stenosis model needs to be able to estimate the patient's heart period from the video clip. Moreover, the clip length must be greater or equal than the heart period, to make sure at least one full heart cycle is present.

Predicting the Patient's Heart Period

The example aortic stenosis model has the ability to predict a patient's heart period by looking solely at the video clip. To achieve this, the model was trained to predict, on each frame, the coordinates of a point on a unit circle corresponding to that frame's exact moment in the heart cycle. The circle was defined by arbitrarily associating the R-wave of the EKG to the point of coordinates (1, 0). For each intermediate time point between 2 consecutive R-waves with timestamps and (cos( ), sin( )) coordinates were assigned to that point by a simple interpolation in time.

Figure 7:
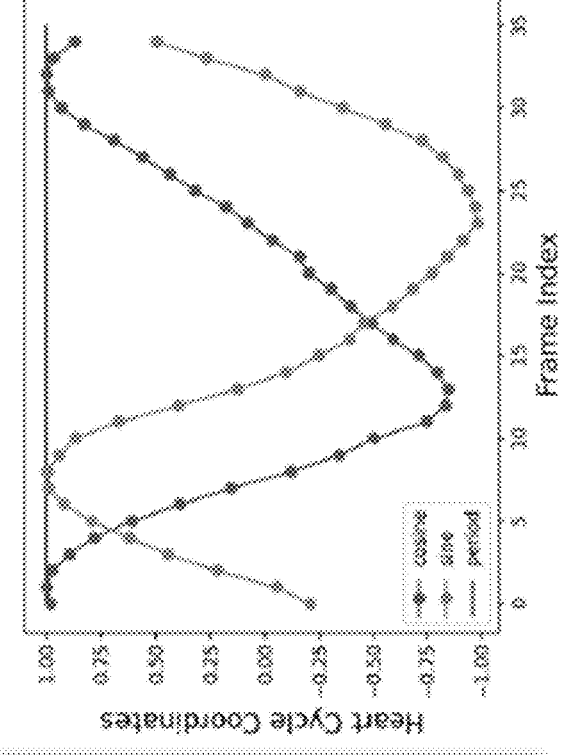
FIG. 7 illustrates (left) an example frame (frame #5) from an example video clip comprising a plurality of ultrasound images of a parasternal long axis (PLAX) view of a heart together with (right) a graph showing predicted heart cycle coordinates determined using an example model implemented according to the workflow illustrated in FIG. 3.
Figure 7:
Figure 8:
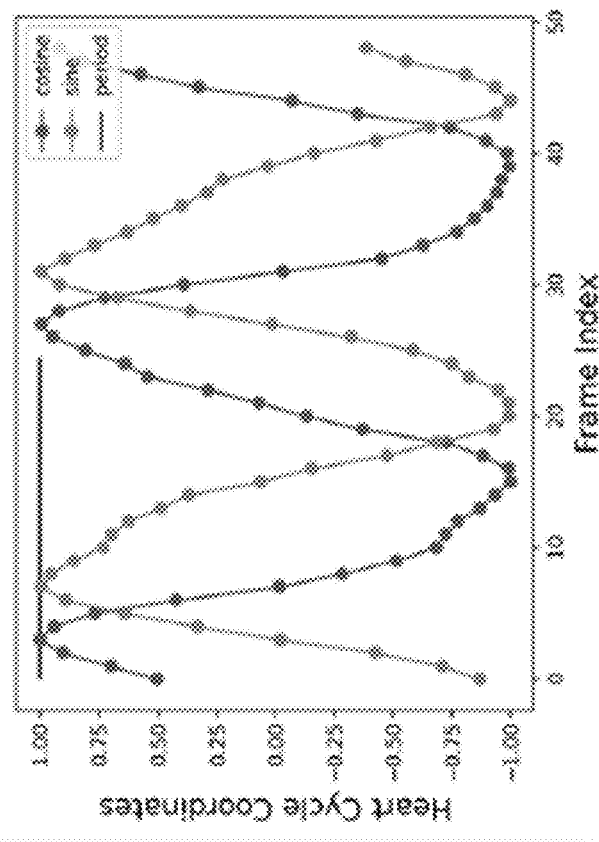
FIG. 8 illustrates (left) an example frame (frame #5) from an example video clip comprising a plurality of ultrasound images of a parasternal short axis aortic valve (PSAX-AoV) view of a heart together with (right) a graph showing predicted heart cycle coordinates determined using an example model implemented according to the workflow illustrated in FIG. 3.
Figure 8:

Given an input video clip, the example aortic stenosis model returns two time series corresponding to estimated heart cycle coordinates on each frame. Shown in FIGS. 7-8 are two examples of predicted time series of heart cycle coordinates, predicted heart period (the horizontal red line) along with one random frame extracted from the clip. To go from estimated heart cycle coordinates to heart period, the following post-processing operations are applied to each time series separately:

1. A Fast Fourier Transform (FFT) of the time series is applied to obtain Fourier coefficients.
2. The Fourier frequencies associated with these coefficients are extracted.
3. The modulus of each Fourier coefficients is taken (to make them positive).
4. A softmax operation is applied to the vector of Fourier coefficients to obtain a normalized probability-like distribution of weights.
5. A weighted average of the Fourier frequencies is computed using the normalized vector of weights from 4. The heart period is then obtained by taking the inverse of the average frequency.

This produces two estimates for the heart period, one from the post-processing of the cosine time series and another from the post-processing of the sine time series. The final heart period estimate as implemented in the example annotator is then obtained by averaging these two quantities.

Converting From an Image Clip to Confidence Distributions Over AS Severities The example aortic stenosis model operates on windows of 24 contiguous frames. Given an input 24-frame long sequence, the example aortic stenosis model returns 4 positive numbers that sum up to 1 that is referred to as a confidence distribution. These numbers represent the assurance the model has in ascribing the input sequence to any of 4 aortic stenosis severity levels implemented in the example (namely "none", "mild", "moderate" and "severe"). Given an image clip containing N frames (assuming N≥24), a 24-frame long window can be slid along the time axis and a total of (N−24+1) sequences can be extracted. For each sequence, the example aortic stenosis model returns a confidence distribution.

In order to produce confidence distributions that make sense from a medical standpoint, these distributions often need to be averaged over one or more heart periods. For that, the heart period T can be determined on each clip individually using the procedure described in the previous subsection. For the example model, that period spans exactly Δ(T−24+1)24-frame long windows (assuming T≥24). Consequently, the example aortic stenosis model's confidence distributions are averaged over A windows to produce a total of N−T+1 predictions.

To obtain confidence distributions on combination of views (i.e., combination of heart periods from two or more distinct cardiac views), each heart period's confidence distribution is extracted as outlined herein, and then considered based on their cartesian product. Each element of the product consists of a tuple of two or more confidence distributions. To obtain a combined confidence distribution, the tuple's individual distributions are averaged together. To return an aortic stenosis severity classification given a confidence distribution, the severity with the highest confidence can be returned.

Quantifying the Probability of a Successful Classification

Beyond producing an estimate of aortic stenosis severity (or other pathology), the example aortic stenosis model can quantify the probability of producing a successful classification. Any such "confidence" measure can be defined in a statistical sense to observe how well the model performs on a large enough dataset of held out patients and then hopefully find an appropriate space of features that can separate the example aortic stenosis model's performance into different regimes.

Two features were used for this purpose in the example aortic stenosis model. The first feature is straightforward and corresponds to the maximum value of the example aortic stenosis model's confidence distribution (see FIG. 2). This feature is called the top confidence. The second feature quantifies how concentrated around the maximum value a distribution is and penalizes distributions that have secondary peaks. This second feature is called the unimodality score.

Figure 9:
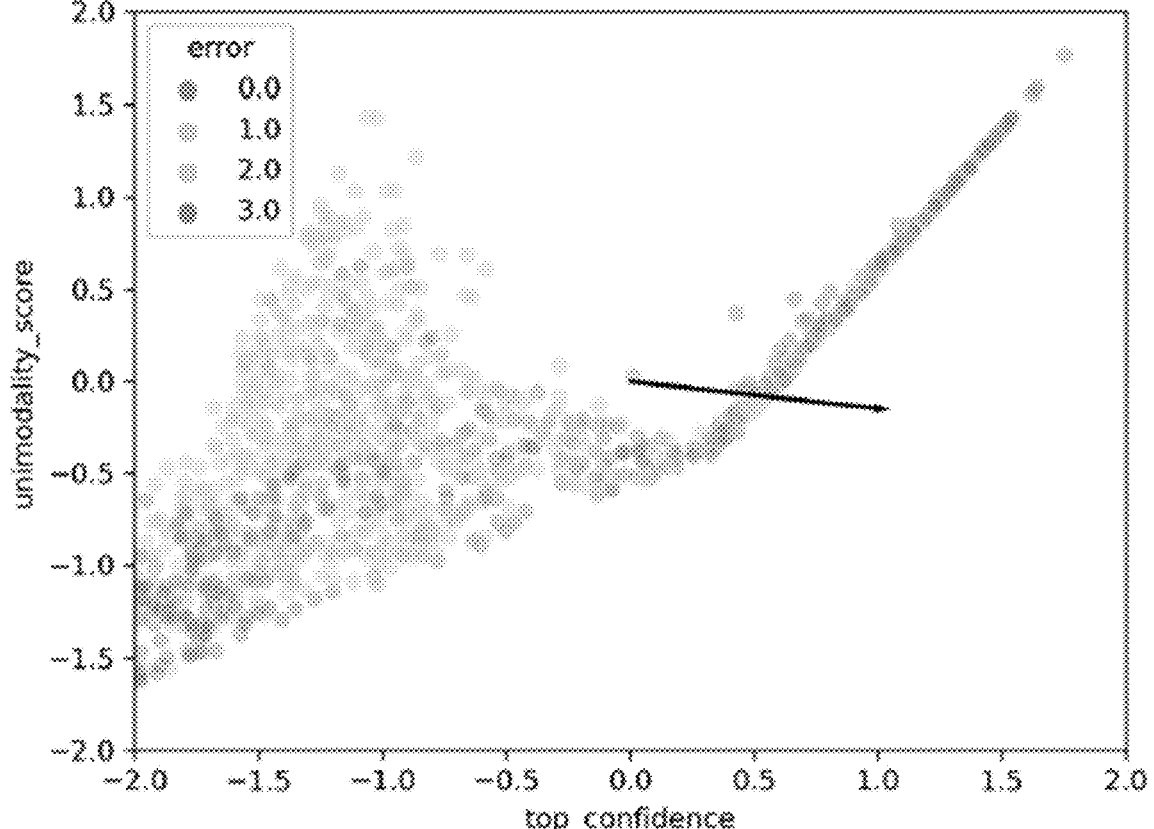
FIG. 9 illustrates a scatter plot of observed errors in classification of aortic stenosis by an example model implemented according to the workflow illustrated in FIG. 3.
Figure 10:
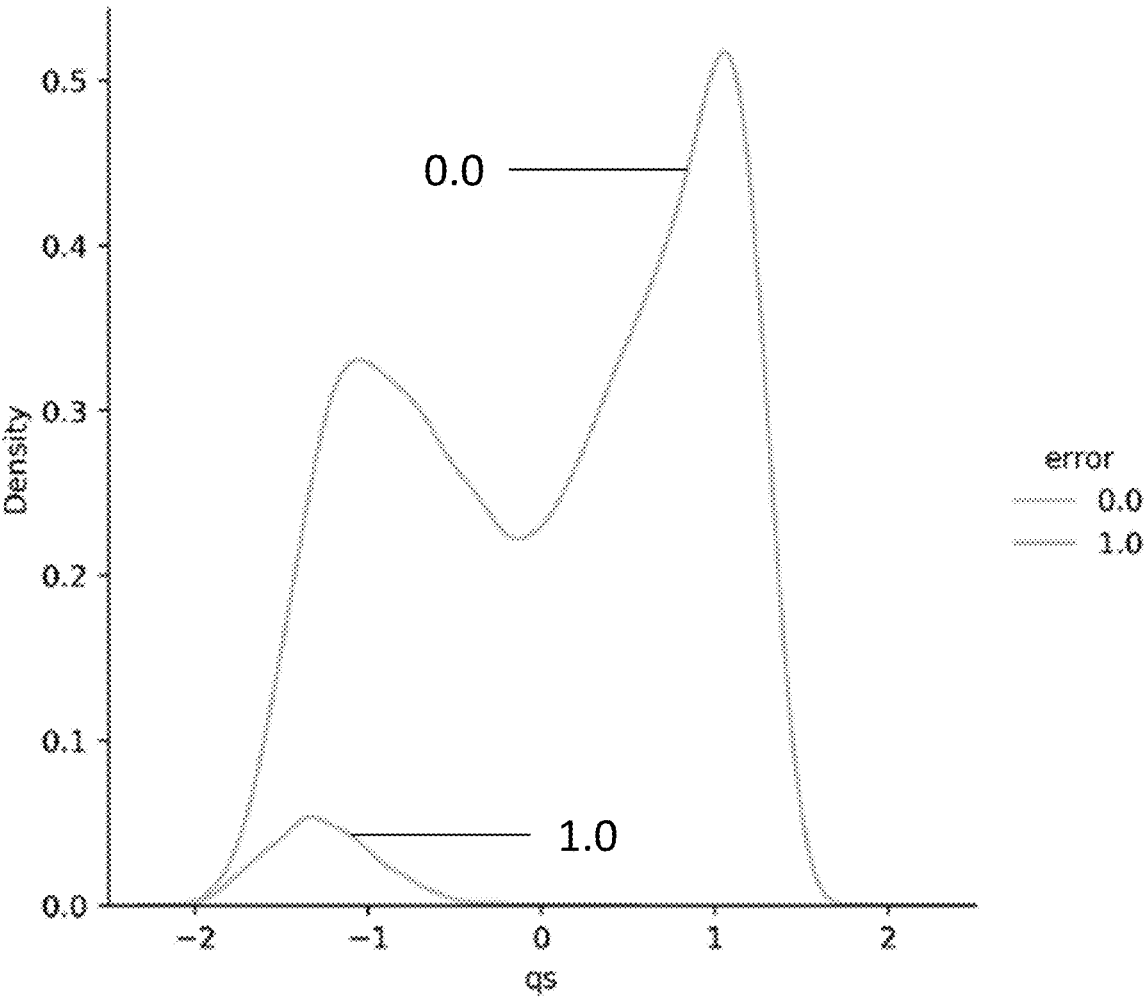
FIG. 10 illustrates data density plotted against quality score for an example binary prediction task using an example model implemented according to the workflow illustrated in FIG. 3. The data density can help to model how well the example model can be expected to perform on a binary prediction task as a function of quality score (QS). A fit was performed using a maximum likelihood procedure, a model logistic regression classifier to the binary problem (classify whether we make a successful binary prediction for None/Mild vs Moderate/Severe) using a single feature as input: quality score. The model is assumed to reduce to a random chance of 50% when quality scores are low and lead to perfect accuracy (100%) when quality scores are high. Moreover the classifier has only 2 free parameters, namely a scaling factor and an intercept.

For any given prediction, the example aortic stenosis model can either be correct (error 0), be 1 severity level away (error 1), 2 severity levels away (error 2) or 3 severity levels away (error 3). The evaluation set described herein (minus a subset of 40 patients that were kept separate for a Pilot study) was used to visualize how the model's errors were distributed in feature space. FIG. 9 displays, for each error type (error 0, 1, 2 or 3), 400 random representative samples (note that prior to plotting, features have been standardized to have zero mean and unit standard deviation). The black arrow on that plot displays a direction of "optimal separability" of the errors. FIG. 9 illustrates a scatter plot of the example aortic stenosis model's errors in feature space. If every data point is projected in our evaluation set along this optimal direction, a scalar for each of these examples that called a quality score (QS) is obtained. FIG. 10 shows the normalized data density for a binary prediction task None/Mild vs Moderate/Severe in the evaluation dataset as a function of QS.

Multiple conclusions can be inferred from FIG. 10. First, the example model produces a correct binary prediction most of the time. Second, the high QS values are associated with a high probability of making no errors, while low QS values are associated with a higher probability of making an error.

Figure 11:
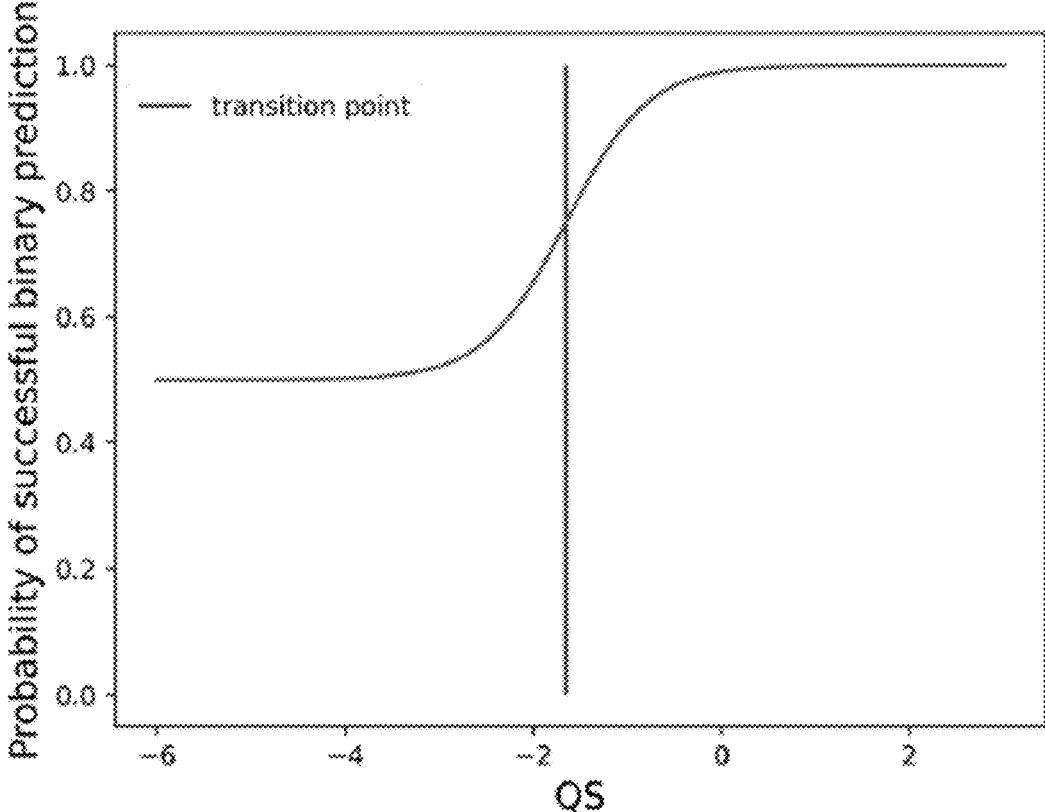
FIG. 11 illustrates the result of a fit performed on the data of FIG. 10.

FIG. 10 illustrates data density plotted against quality score for a binary prediction task. How well the example aortic stenosis model can be expected to perform on this binary prediction task as a function of QS can be modeled using this data. Using a maximum likelihood procedure, a model logistic regression classifier can be fit to the binary problem (classify whether we make a successful binary prediction for None/Mild vs Moderate/Severe) using a single feature as input: quality score. The model is assumed to reduce to a random chance of 50% when quality scores are low and lead to perfect accuracy (100%) when quality scores are high. Moreover the classifier has only 2 free parameters, namely a scaling factor and an intercept. The result of the fit is shown in FIG. 11 which illustrates a logistic regression classifier probability profile against quality score.

Figure 3:
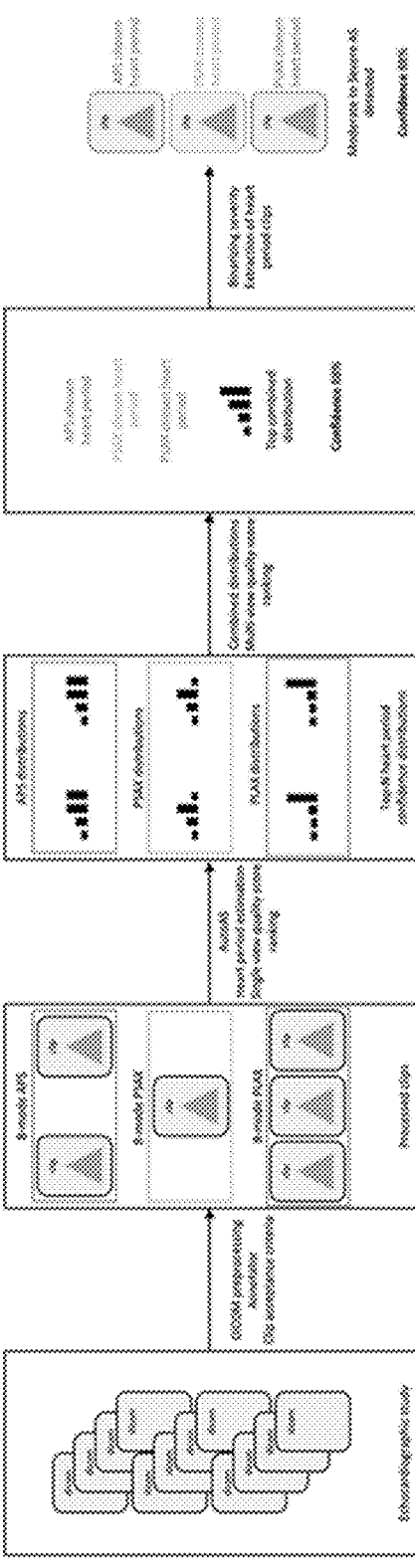
FIG. 3 illustrates a detailed schematic workflow of an example implementation of methods and systems described herein.

In some cases, this "probability of success" can be used as a definition of confidence in the example aortic stenosis model's prediction. FIG. 3 summarizes the example model workflow. For example, echocardiographic studies can be performed on a large group of patients to accumulate DICOM files comprising images of a plurality of views of each patient's heart. Preprocessing can then be performed to annotate clips comprised in one or more of the DICOM files to yield processed clips. The processed clips can then be submitted to a confidence algorithm and/or a confidence machine learning model which estimates the heart period and/or a single view quality score for one or more (e.g. for each) of the clips. The annotated clips can then be ranked by one or more of these parameters to yield a distribution of clips of each view producing the highest confidence for classification of a pathology of an organ of the patient (e.g. aortic stenosis). The algorithm or machine learning model may then combine insight gained from clips having the highest prediction confidence to determine a combined confidence distribution based at least in part on a subset of each individual view, and/or by selecting an optimized subset of views computed or predicted to provide the highest confidence for classification of the pathology to be measured.

Subsequent images can then be submitted to the example model workflow for assessment of a pathology of a newly imaged subject (e.g. for diagnosis of aortic stenosis in a patient in a clinical setting). Output parameters from the model workflow can include presence or absence of the pathology, a severity of the pathology (e.g. aortic stenosis) in a submitted image, a confidence of the model prediction in either the presence/absence and/or the severity, and/or combinations thereof.

Figure 4:
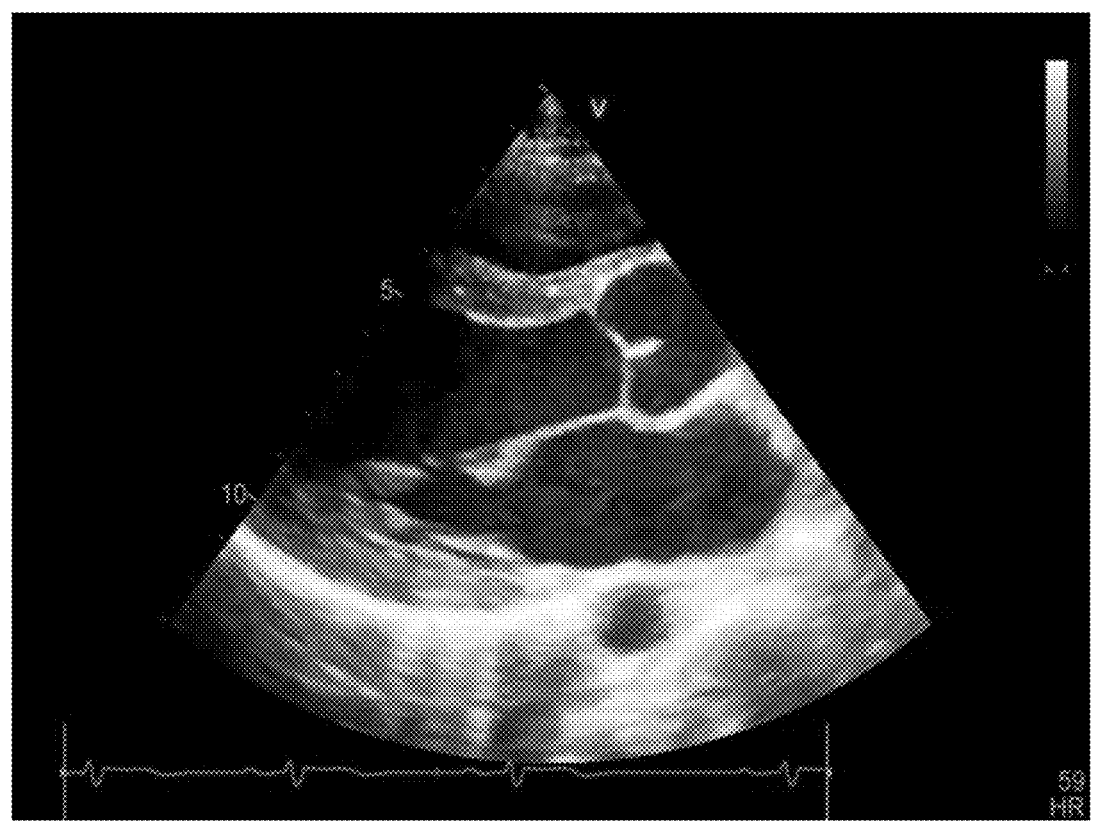
FIG. 4 illustrates an example ultrasound image of a parasternal long axis view of the heart of a healthy subject. The view shows the normal aortic valve, with thin leaflets and no calcification, the left ventricle, and left atrium, mitral valve, etc.
Figure 5:
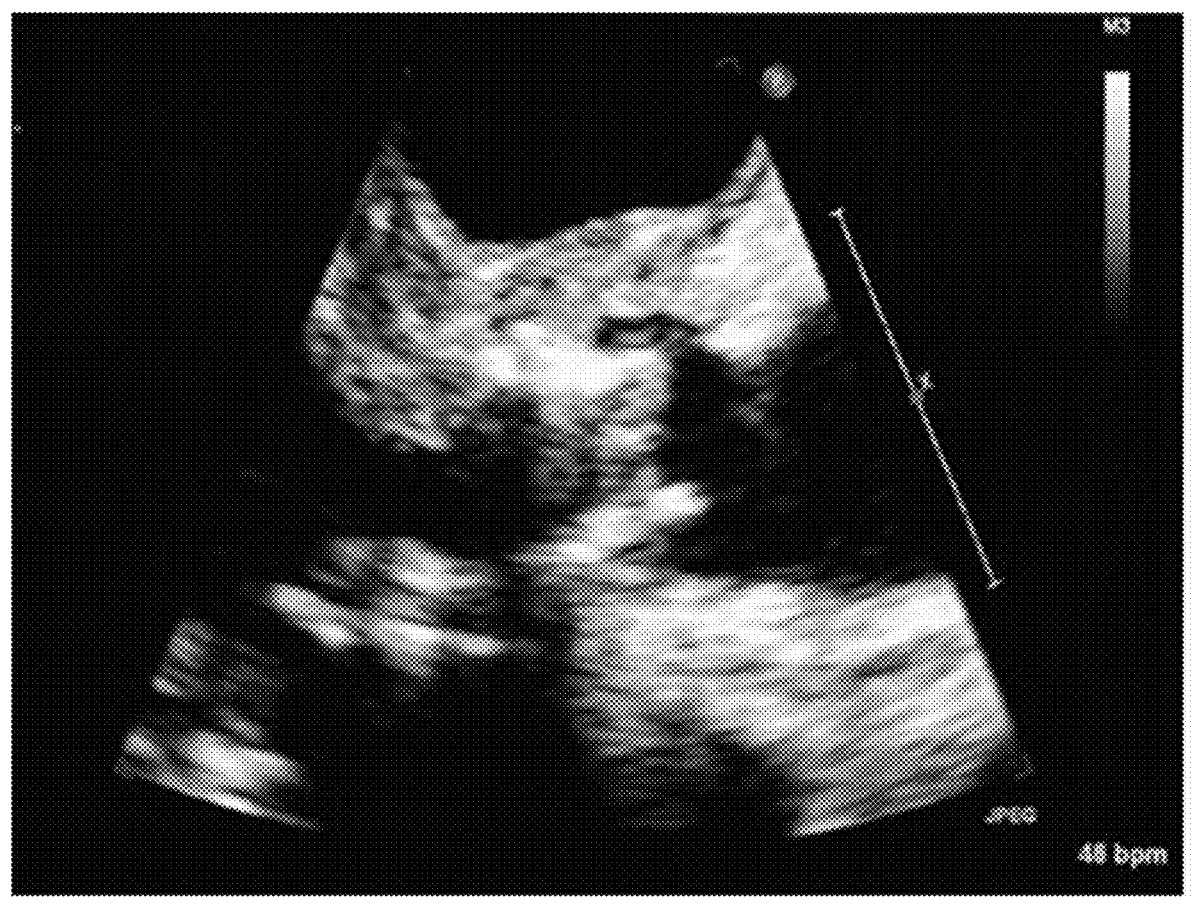
FIG. 5 illustrates an example ultrasound image focused on a stenotic aortic valve. It is highly diagnostic for aortic stenosis, but does not contain the full set of anatomical targets of the standard canonical parasternal long axis view. A clip selector not trained to select images that are missing those features, or not trained to select images that have indications of pathologies could reject such an image and not process it. Methods and systems described herein are able to process such clips, for example, using methods for classifying pathologies such as aortic stenosis described herein.

For example, an ultrasound image of a parasternal long axis view of a healthy heart such as the one shown in FIG. 4, would produce a high confidence value for a result indicating the absence (or no/low severity) when evaluated for aortic stenosis since the view shows a normal aortic valve, with thin leaflets and no calcification, the left ventricle, and left atrium, mitral valve, which all appear normal. In contrast, an ultrasound image of a stenotic aortic valve, such as that illustrated in FIG. 5 would yield a high confidence level for a prediction or classification that a severe aortic stenosis is present (e.g. the output may comprise an indication that severe aortic stenosis is present with a confidence level of 95% or more), despite that the image shown does not contain the full set of anatomical targets of the standard canonical parasternal long axis view (the absence of which can often confuse quality assessment algorithms and models).

Use of a large plurality of views in the training data (including sub-views which comprise non-canonical views) can provide the example model with substantially improved robustness in classifying aortic stenosis compared to methods which require visual detection of a valve opening and/or a valve closure within an ultrasound image clip. In some cases, the example model is able to classify aortic stenosis without a visual detection of valve opening and/or closing within a classified clip.

Machine Learning Algorithms

Disclosed herein are platforms, systems, and methods that provide ultrasound image classification using machine learning algorithm(s). In particular, in some aspects, the machine learning algorithms include deep learning neural networks configured for evaluating ultrasound images. The algorithms can include one or more of a positioning algorithm, a scoring algorithm, a probe guidance algorithm, and an intrinsic image quality algorithm. The positioning algorithm can include one or more neural networks that estimate probe positioning relative to an ideal anatomical view or perspective and/or a distance or deviation of a current probe position from an ideal probe position. The intrinsic image quality algorithm may determine that intrinsic image quality is below a threshold based in part on a determination by a positioning algorithm that one or more images have been acquired at a probe position expected to obtain a clinical quality image.

The development of each machine learning algorithm spans three phases: (1) dataset creation and curation, (2) algorithm training, and (3) adapting design elements necessary for product performance and useability. The dataset used for training the algorithm can be generated by obtaining ultrasound images that are then curated and labeled by expert radiologists, for example, according to positioning, score, and other metrics. Each algorithm then undergoes training using the training dataset, which can include one or more different target organs and/or one or more different views of a given target organ. The training dataset for the positioning algorithm may be labeled according to a known probe pose deviation from the optimal probe pose. A non-limiting description of the training and application of a positioning algorithm or estimator can be found in U.S. patent application Ser. No. 15/831,375, the entirety of which is hereby incorporated by reference. Another non-limiting description of a positioning algorithm and a probe guidance algorithm can be found in U.S. patent application Ser. No. 16/264,310, the entirety of which is hereby incorporated by reference. The design elements can include a user interface comprising an omnidirectional guidance feature.

A machine learning model can comprise a supervised, semi-supervised, unsupervised, or self-supervised machine learning model. In some cases, the one or more ML approaches perform classification or clustering of the MS data. In some examples, the machine learning approach comprises a classical machine learning method, such as, but not limited to, support vector machine (SVM) (e.g., one-class SVM, linear or radial kernels, etc.), K-nearest neighbor (KNN), isolation forest, random forest, logistic regression, AdaBoost classifier, extra trees classifier, extreme gradient boosting, gaussian process classifier, gradient boosting classifier, light gradient boosting, linear discriminant analysis, naïve Bayes, quadratic discriminant analysis, ridge classifier, or any combination thereof. In some examples, the machine learning approach comprises a deep leaning method (e.g., deep neural network (DNN)), such as, but not limited to a fully-connected network, convolutional neural network (CNN) (e.g., one-class CNN), recurrent neural network (RNN), transformer, graph neural network (GNN), convolutional graph neural network (CGNN), multi-level perceptron (MLP), or any combination thereof.

In some aspects, a classical ML method comprises one or more algorithms that learns from existing observations (i.e., known features) to predict outputs. In some aspects, the one or more algorithms perform clustering of data. In some examples, the classical ML algorithms for clustering comprise K-means clustering, mean-shift clustering, density-based spatial clustering of applications with noise (DB-SCAN), expectation-maximization (EM) clustering (e.g., using Gaussian mixture models (GMM)), agglomerative hierarchical clustering, or any combination thereof. In some aspects, the one or more algorithms perform classification of data. In some examples, the classical ML algorithms for classification comprise logistic regression, naïve Bayes, KNN, random forest, isolation forest, decision trees, gradient boosting, support vector machine (SVM), or any combination thereof. In some examples, the SVM comprises a one-class SMV or a multi-class SVM.

In some aspects, the deep learning method comprises one or more algorithms that learns by extracting new features to predict outputs. In some aspects, the deep learning method comprises one or more layers. In some aspects, the deep learning method comprises a neural network (e.g., DNN comprising more than one layer). Neural networks generally comprise connected nodes in a network, which can perform functions, such as transforming or translating input data. In some aspects, the output from a given node is passed on as input to another node. The nodes in the network generally comprise input units in an input layer, hidden units in one or more hidden layers, output units in an output layer, or a combination thereof. In some aspects, an input node is connected to one or more hidden units. In some aspects, one or more hidden units is connected to an output unit. The nodes can generally take in input through the input units and generate an output from the output units using an activation function. In some aspects, the input or output comprises a tensor, a matrix, a vector, an array, or a scalar. In some aspects, the activation function is a Rectified Linear Unit (ReLU) activation function, a sigmoid activation function, a hyperbolic tangent activation function, or a Softmax activation function.

The connections between nodes further comprise weights for adjusting input data to a given node (i.e., to activate input data or deactivate input data). In some aspects, the weights are learned by the neural network. In some aspects, the neural network is trained to learn weights using gradient-based optimizations. In some aspects, the gradient-based optimization comprises one or more loss functions. In some aspects, the gradient-based optimization is gradient descent, conjugate gradient descent, stochastic gradient descent, or any variation thereof (e.g., adaptive moment estimation (Adam)). In some further aspects, the gradient in the gradient-based optimization is computed using backpropagation. In some aspects, the nodes are organized into graphs to generate a network (e.g., graph neural networks). In some aspects, the nodes are organized into one or more layers to generate a network (e.g., feed forward neural networks, convolutional neural networks (CNNs), recurrent neural networks (RNNs), etc.). In some aspects, the CNN comprises a one-class CNN or a multi-class CNN.

In some aspects, the neural network comprises one or more recurrent layers. In some aspects, the one or more recurrent layers are one or more long short-term memory (LSTM) layers or gated recurrent units (GRUs). In some aspects, the one or more recurrent layers perform sequential data classification and clustering in which the data ordering is considered (e.g., time series data). In such aspects, future predictions are made by the one or more recurrent layers according to the sequence of past events. In some aspects, the recurrent layer retains or "remembers" important information, while selectively "forgets" what is not essential to the classification.

In some aspects, the neural network comprise one or more convolutional layers. In some aspects, the input and the output are a tensor representing variables or attributes in a data set (e.g., features), which may be referred to as a feature map (or activation map). In such aspects, the one or more convolutional layers are referred to as a feature extraction phase. In some aspects, the convolutions are one dimensional (1D) convolutions, two dimensional (2D) convolutions, three dimensional (3D) convolutions, or any combination thereof. In further aspects, the convolutions are 1D transpose convolutions, 2D transpose convolutions, 3D transpose convolutions, or any combination thereof.

The layers in a neural network can further comprise one or more pooling layers before or after a convolutional layer. In some aspects, the one or more pooling layers reduces the dimensionality of a feature map using filters that summarize regions of a matrix. In some aspects, this down samples the number of outputs, and thus reduces the parameters and computational resources needed for the neural network. In some aspects, the one or more pooling layers comprises max pooling, min pooling, average pooling, global pooling, norm pooling, or a combination thereof. In some aspects, max pooling reduces the dimensionality of the data by taking only the maximums values in the region of the matrix. In some aspects, this helps capture the most significant one or more features. In some aspects, the one or more pooling layers is one dimensional (1D), two dimensional (2D), three dimensional (3D), or any combination thereof.

The neural network can further comprise of one or more flattening layers, which can flatten the input to be passed on to the next layer. In some aspects, a input (e.g., feature map) is flattened by reducing the input to a one-dimensional array. In some aspects, the flattened inputs can be used to output a classification of an object. In some aspects, the classification comprises a binary classification or multi-class classification of visual data (e.g., images, videos, etc.) or non-visual data (e.g., measurements, audio, text, etc.). In some aspects, the classification comprises binary classification of an image (e.g., contrast needed or contrast not needed). In some aspects, the classification comprises multi-class classification of a text (e.g., identifying hand-written digits)). In some aspects, the classification comprises binary classification of a measurement. In some examples, the binary classification of a measurement comprises a classification of a system's performance using the physical measurements described herein (e.g., normal or abnormal, normal or anormal).

The neural networks can further comprise of one or more dropout layers. In some aspects, the dropout layers are used during training of the neural network (e.g., to perform binary or multi-class classifications). In some aspects, the one or more dropout layers randomly set some weights as 0 (e.g., about 10%, 20%, 30%, 40%, 50%, 60%, 70%, 80% of weights). In some aspects, the setting some weights as 0 also sets the corresponding elements in the feature map as 0. In some aspects, the one or more dropout layers can be used to avoid the neural network from overfitting.

The neural network can further comprise one or more dense layers, which comprises a fully connected network. In some aspects, information is passed through a fully connected network to generate a predicted classification of an object. In some aspects, the error associated with the predicted classification of the object is also calculated. In some aspects, the error is backpropagated to improve the prediction. In some aspects, the one or more dense layers comprises a Softmax activation function. In some aspects, the Softmax activation function converts a vector of numbers to a vector of probabilities. In some aspects, these probabilities are subsequently used in classifications, such as classifications of a pathology according to any of the methods or systems described herein.

Computer Systems

Figure 12:
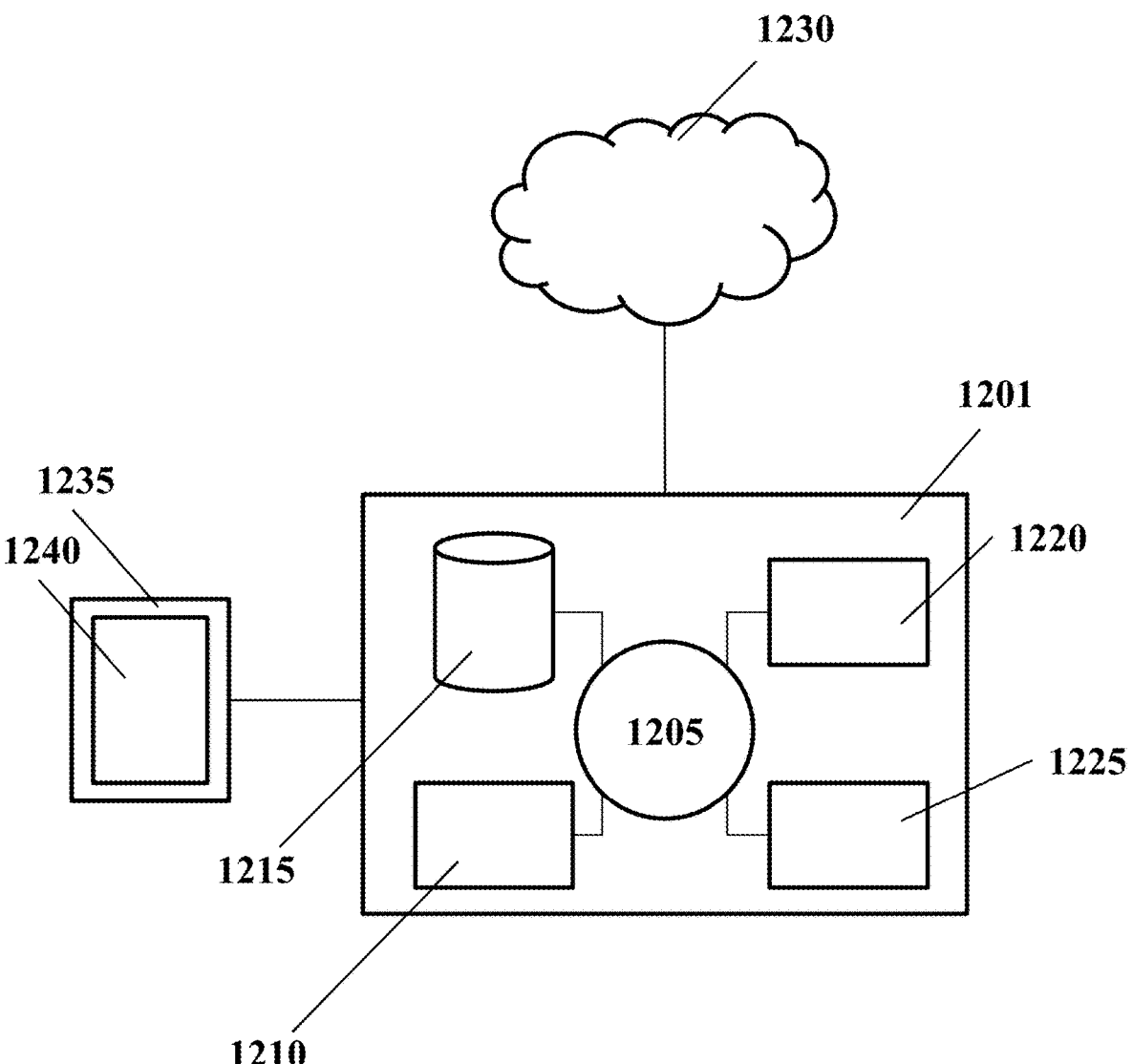
FIG. 12 shows a computer system that is programmed or otherwise configured to implement methods provided herein.

The present disclosure provides computer systems that are programmed to implement methods of the disclosure. FIG. 12 shows a computer system 1201 that is programmed or otherwise configured to assess one or more pathologies based on an ultrasound image using any of the methods or systems described herein. The computer system 1201 can regulate various aspects of the present disclosure, such as, for example, computing a severity and a confidence of one or more pathologies based on an ultrasound image and/or alerting the user to the severity and corresponding confidence. In some instances, the computer system 1201 can be an electronic device of a user or a computer system that is remotely located with respect to the electronic device. The electronic device can be a mobile electronic device.

The computer system 1201 includes a central processing unit (CPU, also "processor" and "computer processor" herein) 1205, which can be a single core or multi core processor, or a plurality of processors for parallel processing. The computer system 1201 also includes memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. The memory 1210, storage unit 1215, interface 1220 and peripheral devices 1225 are in communication with the CPU 1205 through a communication bus (solid lines), such as a motherboard. The storage unit 1215 can be a data storage unit (or data repository) for storing data. The computer system 1201 can be operatively coupled to a computer network ("network") 1230 with the aid of the communication interface 1220. The network 1230 can be the Internet, an internet and/or extranet, or an intranet and/or extranet that is in communication with the Internet. The network 1230 in some cases is a telecommunication and/or data network. The network 1230 can include one or more computer servers, which can enable distributed computing, such as cloud computing. The network 1230, in some cases with the aid of the computer system 1201, can implement a peer-to-peer network, which may enable devices coupled to the computer system 1201 to behave as a client or a server.

The CPU 1205 can execute a sequence of machine-readable instructions, which can be embodied in a program or software. The instructions may be stored in a memory location, such as the memory 1210. The instructions can be directed to the CPU 1205, which can subsequently program or otherwise configure the CPU 1205 to implement methods of the present disclosure. Examples of operations performed by the CPU 1205 can include fetch, decode, execute, and writeback.

The CPU 1205 can be part of a circuit, such as an integrated circuit. One or more other components of the system 1201 can be included in the circuit. In some cases, the circuit is an application specific integrated circuit (ASIC).

The storage unit 1215 can store files, such as drivers, libraries and saved programs. The storage unit 1215 can store user data, e.g., user preferences and user programs. The computer system 1201 in some cases can include one or more additional data storage units that are external to the computer system 1201, such as located on a remote server that is in communication with the computer system 1201 through an intranet or the Internet.

The computer system 1201 can communicate with one or more remote computer systems through the network 1230. For instance, the computer system 1201 can communicate with a remote computer system of a user (e.g., a family physician, an untrained technician, a patient, and/or a cardiologist or other specialist). Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 1201 via the network 1230.

Methods as described herein can be implemented by way of machine (e.g., computer processor) executable code stored on an electronic storage location of the computer system 1201, such as, for example, on the memory 1210 or electronic storage unit 1215. The machine executable or machine-readable code can be provided in the form of software. During use, the code can be executed by the processor 1205. In some cases, the code can be retrieved from the storage unit 1215 and stored on the memory 1210 for ready access by the processor 1205. In some situations, the electronic storage unit 1215 can be precluded, and machine-executable instructions are stored on memory 1210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1201, can be embodied in programming. Various aspects of the technology may be thought of as "products" or "articles of manufacture" typically in the form of machine (or processor) executable code and/or associated data that is carried on or embodied in a type of machine-readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1201 can include or be in communication with an electronic display 1235 that comprises a user interface (UI) 1240 for providing, for example, a user interface providing a readout of the severity and confidence of the presence of one or more pathology in real time. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1205. The algorithm can, for example, implement any of the methods or facilitate the operation of any of the systems described herein.

EXAMPLES

The following illustrative examples are representative of aspects of the software applications, systems, and methods described herein and are not meant to be limiting in any way.

Example 1 Automatic Classification of a Pathology During an Ultrasound Imaging Procedure A sonographer acquires ultrasound images of a patient according to methods and/or using systems described herein. While the stenographer is collecting images, the ultrasound imaging system implementing methods described herein is processing the images and assessing the severity of one or more pathologies (such as aortic stenosis). The system then provides the stenographer with an estimate of the severity of one or more pathologies effecting the subject, together with an estimate of the confidence of the estimate.

While preferred aspects of the present invention have been shown and described herein, it will be obvious to those skilled in the art that such aspects are provided by way of example only. It is not intended that the invention be limited by the specific examples provided within the specification. While the invention has been described with reference to the aforementioned specification, the descriptions and illustrations of the aspects herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the aspects of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

The invention claimed is:

1. An ultrasound imaging system comprising:

an ultrasound imaging probe;

a computing system; and a non-transitory computer-readable storage medium, storing instructions that, when executed by a processor of the computing system cause the ultrasound imaging system to:

acquire, by the ultrasound imaging probe, a plurality of ultrasound images of a subject;

process the acquired plurality of ultrasound images to automatically classify a pathology of the subject; and output an indication of a condition of the subject, the output comprising: (i) an indication of a severity of the pathology in the subject; and (ii) a confidence estimate of the indication of (i), wherein one or more video clips comprise the plurality of ultrasound images, wherein each of the one or more video clips is associated with one or more discrete views, and estimating the severity of the pathology comprises:

(I) for each of the one or more video clips:

determining a heart period of the subject of the video clip;

sliding a window of a size based on the determined heart period over the clip; and computing a confidence distribution and/or an associated likelihood of successful severity classification for the pathology;

(II) extracting windows associated with the one or more video clips which meet a threshold value for likelihood of successful severity classification; and (III) combining the extracted windows from two or more of the one or more discrete views to obtain an increased likelihood of successful severity classification compared with classification based on an individual one of the discrete views.

2. A method for ultrasound imaging, the method comprising:

processing a plurality of ultrasound images to automatically classify a pathology of a subject; and outputting an indication of a condition of the subject, the output comprising: (i) an indication of a severity the pathology in the subject; and (ii) a confidence estimate of the indication of (i), wherein one or more video clips comprise the plurality of ultrasound images, wherein each of the one or more video clips is associated with one or more discrete views, and estimating the severity of the pathology comprises:

(I) for each of the one or more video clips:

determining a heart period of the subject of the video clip;

sliding a window of a size based on the determined heart period over the clip; and computing a confidence distribution and/or an associated likelihood of successful severity classification for the pathology;

(II) extracting windows associated with the one or more video clips which meet a threshold value for likelihood of successful severity classification; and (III) combining the extracted windows from two or more of the one or more discrete views to obtain an increased likelihood of successful severity classification compared with classification based on an individual one of the discrete views.

3. The method of claim 2, wherein the pathology is aortic stenosis.

4. The method of claim 2, wherein the method for ultrasound imaging does not comprise visual detection of a heart valve closure within the acquired plurality of images.

5. The method of claim 2, wherein the automatic classification is performed on at least a subset of the plurality of ultrasound images which are substandard images.

6. The method of claim 2, wherein estimating the severity of the pathology further comprises:

ranking the windows for all clips associated with a particular view based on likelihood of successful severity classification to obtain a subset containing less than all of the windows associated with the particular view, which comprises three or more windows associated with the particular view which have the highest likelihood of successful severity classification; and after the combining of (III), re-ranking the windows for all of the combined clips based on likelihood of successful severity classification to obtain a combination of windows having a highest global likelihood of successful severity classification.

7. The method of claim 2, wherein the output comprises an instruction of a user of an ultrasound system to acquire further images of the subject.

8. The method of claim 7, wherein the instruction to acquire further images is provided based at least in part on a detection of at least a threshold likelihood of a presence of the pathology in one or more of the plurality of ultrasound images.

9. The method of claim 7, wherein the instruction to acquire further images is provided based at least in part on a detection that less than a threshold confidence in the presence or absence of the pathology is detected.

10. The method of claim 9, wherein the plurality of ultrasound images are two-dimensional ultrasound images.

11. A non-transitory computer-readable medium, storing instructions that, when executed by a processor of a computer, cause the computer to:

(a) process a plurality of ultrasound images to automatically classify a pathology of a subject; and (b) output, an indication of a condition of the subject, the output comprising: (i) an indication of a severity of the pathology in the subject; and (ii) a confidence estimate of the indication of (i), wherein one or more video clips comprise the plurality of ultrasound images, wherein each of the one or more video clips is associated with one or more discrete views, and estimating the severity of the pathology comprises:

(I) for each of the one or more video clips:

determining a heart period of the subject of the video clip;

sliding a window of a size based on the determined heart period over the clip; and computing a confidence distribution and/or an associated likelihood of successful severity classification for the pathology;

(II) extracting windows associated with the one or more video clips which meet a threshold value for likelihood of successful severity classification; and (III) combining the extracted windows from two or more of the one or more discrete views to obtain an increased likelihood of successful severity classification compared with classification based on an individual one of the discrete views.

\* \* \* \* \*